United States Patent [19]

Farmer, III et al.

[11] 4,304,691
[45] Dec. 8, 1981

[54] AQUEOUS HAIR SHAMPOO COMPOSITIONS COMPRISING SULFATED ETHYLENE OXIDE-PROPYLENE OXIDE CONDENSATES

[75] Inventors: Robert F. Farmer, III, Rockville, Md.; Jacob J. Guth, Upper Black Eddy, Pa.

[73] Assignee: The Gillette Company, Boston, Mass.

[21] Appl. No.: 149,829

[22] Filed: May 15, 1980

Related U.S. Application Data

[62] Division of Ser. No. 97,292, Nov. 26, 1979, abandoned.

[51] Int. Cl.$^3$ ............................ C11D 1/12; C11D 1/83
[52] U.S. Cl. ...................................... 252/545; 252/547; 252/551; 252/DIG. 13; 252/DIG. 14; 260/458 R
[58] Field of Search ....... 252/551, DIG. 13, DIG. 14, 252/547, 353; 260/458 R

[56] References Cited

U.S. PATENT DOCUMENTS

| | | | |
|---|---|---|---|
| 3,086,943 | 4/1963 | Lang | 252/551 X |
| 3,931,271 | 1/1976 | Baumann et al. | 260/458 |
| 4,064,076 | 12/1977 | Klisch et al. | 252/542 |
| 4,070,309 | 1/1978 | Jacobsen | 252/547 |
| 4,077,917 | 3/1978 | Panzer | 252/545 |
| 4,144,201 | 3/1979 | Winterbottom et al. | 252/547 |
| 4,212,749 | 7/1980 | Kolbe | 252/8.75 |

*Primary Examiner*—P. E. Willis, Jr.
*Attorney, Agent, or Firm*—Leonard J. Janowski

[57] ABSTRACT

This invention deals with novel sulfated condensation products of ethylene oxide with bases formed by condensing propylene oxide with propylene glycol, and having a molecular weight of about $11\phi\phi$ to $48\phi\phi$. The sulfated condensation products are useful as components in hair shampoo systems to provide an after-shampoo conditioning effect.

5 Claims, No Drawings

AQUEOUS HAIR SHAMPOO COMPOSITIONS COMPRISING SULFATED ETHYLENE OXIDE-PROPYLENE OXIDE CONDENSATES

This is a division of application Ser. No. 097,292, filed Nov. 26, 1979, now abandoned.

BACKGROUND

This invention deals with novel sulfated condensation products of ethylene oxide with bases formed by condensing propylene oxide with propylene glycol, and having a molecular weight of about 1100 to 4800. The sulfated condensation products are useful as components in hair shampoo systems to provide an after-shampoo conditioning effect.

The primary function of any hair shampoo product is, of course, to thoroughly remove from the hair accumulated deposits of sebum, airborne particulate materials, and residues of hair treating compositions such as hair sprays or other grooming aids. At least as important, however, from the standpoint of consumer satisfaction are the wet and dry combing properties of the hair after shampooing and the feel and appearance of the hair. As a general rule, shampoos that thoroughly clean the hair tend to leave it hard to comb and in a dry, flyaway condition. Conversely, shampoos which avoid "overdrying" the hair, usually do so at the expense of cleaning effectiveness.

We have discovered a class of materials which when formulated with certain foam promoting agents as will be hereinafter detailed, yield compositions comparable to the better commercially available shampoo compositions in foaming and detergent activity. The compositions of the invention not only impart a smooth, soft feel to the hair, but combing, both wet and dry, is markedly improved.

The prior art describes in, for example, U.S. Pat. No. 2,674,619, methods of making condensation products of ethylene oxide with bases formed by condensing propylene oxide with propylene glycol. We sulfate these condensation products to yield the novel detergents of this invention. The prior art also discloses a family of polyoxypropylene glycol disulfate detergents described as superior heavy-duty fabric detergents having low foaming properties. These materials are shown in U.S. Pat. No. 2,802,789. Also shown in U.S. Pat. No. 3,243,455 is a class of polyether hydroxy sulfonate surface active agents said to be useful in emulsification and demulsification and as components in laundering compositions having good soil anti-redeposition properties. Nowhere in the art, however, is there disclosed the class of sulfated condensation products described herein or the use of such products as components in hair shampoo compositions.

SUMMARY OF THE INVENTION

We have discovered a new class of compounds useful as components in aqueous hair shampoo compositions comprising sulfated condensation products of ethylene oxide with bases formed by condensing propylene oxide with propylene glycol and having a molecular weight of about 1100 to 4800. The members of the class have the following structure:

$$HO-(C_2H_4O)_x(C_3H_6O)_y(C_2H_4O)_z-H$$

where y is an integer from about 30 to 70, preferably about 40 to 60, and $(C_2H_4O)_{x+z}$ equals about 5 to 20% of the total weight of the compound, preferably about 7 to 13%.

DETAILED DESCRIPTION OF THE INVENTION

The class of condensation product precursors which are sulfated in the practice of our invention is a well known class of nonionic surfactant polyols characterized by high molecular weight, predictability of behavior and an extremely low order of toxicity, the molecule having hydrophilic groups at both ends of a variable hydrophobic base. Varying the size of both the hydrophiles and the hydrophobe permits the production of compounds having a mix of properties tailored to the needs of the formulating chemist.

Normally it would be expected that the sulfation of such nonionic species to produce the corresponding anionic materials would result in an increase in skin and/or eye irritation levels when such materials were employed as components in aqueous hair shampoo compositions. We have discovered, however, that the partial or complete sulfation of certain of such condensation products produces cosmetically useful detergent materials retaining the advantageous irritation properties of the nonionic precursor.

The condensation products which we sulfate in the practice of our invention are those having the formula:

$$HO-(C_2H_4O)_x(C_3H_6O)_y(C_2H_4O)_z-H$$

where y is an integer from about 30 to 70, preferably about 40 to 60, and $(C_2H_4O)_{x+z}$ equals about 5 to 20% of the total weight of the compound, preferably about 7 to 13%.

These materials are commercially available in low HLB values of 1 to 4 and when sulfated and neutralized yield water soluble copolymers having an HLB range equivalent to sodium lauryl sulfate.

The preparation of the nonionic surface active polyols which serve as the precursors for the sulfated anionic surface active agents of this invention is well known in the prior art and is described, inter alia, in U.S. Pat. No. 2,674,619. The first step comprises the condensation of propylene oxide with propylene glycol to prepare a polyoxypropylene polymer of at least about 950 molecular weight. This polymer is then condensed with ethylene oxide.

In the first step propylene oxide is condensed with propylene glycol to prepare the polyoxypropylene polymer as follows:

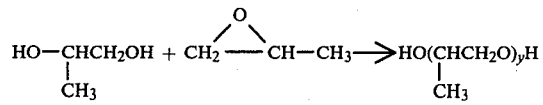

In the second step of the preparation, the polyoxyethylene chain is introduced into the molecule by condensation with ethylene oxide as follows:

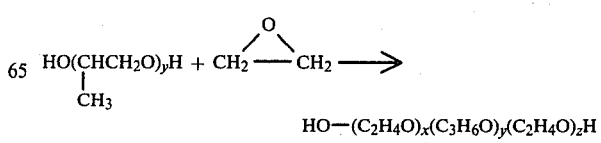

In preparing the polyoxyethylene polymer the condensation of propylene oxide with propylene glycol is normally carried out at elevated temperatures and pressures in the presence of an alkaline catalyst such as sodium alkoxide, a quaternary ammonium base, or preferably sodium hydroxide.

Although the reaction may be carried out by simply heating the mixture of the reactants under pressure at a sufficiently high temperature, this procedure is not ordinarily used as the temperature and pressures required are excessive and control of the reaction is difficult.

The preferred method of carrying out the reaction is to add the propylene oxide to a stirred heated mixture of the propylene glycol and alkaline catalyst in a sealed reaction vessel. By adding the propylene oxide to the reaction vessel at such a rate that it reacts as rapidly as added, an excess of propylene oxide is avoided and control of the reaction is simplified.

The condensation of ethylene oxide with the polyoxypropylene polymer is carried out in an analogous manner.

Partial or complete sulfation of the hydroxyl groups present in the condensation products produced as described above is accomplished through the use of conventional sulfating agents such as those used in the sulfation of fatty alcohol sulfates and their alkoxylated derivatives. These include the various known complexes of sulfur trioxide such as the complexes with dioxane, triethylamine, ammonia and hydrochloric acid. We prefer to sulfate by the slow addition of a hydroxy equivalent of chlorosulfonic acid to a methylene chloride solution of the condensed material. Water dispersible, surface active condensation products are obtained over the range of 0.5 to 2.0 moles of sulfating agent per mole of condensation product. Where hydrophilic condensation products relatively high in ethylene oxide are to be sulfated, concentrations of sulfating agent at the lower end of the range should be employed to retain surface active properties.

The stirred reaction solution is cooled to prevent the temperature from exceeding 25° C. Upon completion of the addition, the solution is sparged with nitrogen to remove any HCl which is present. The sulfuric acid ester is then converted to a salt by pouring the reaction mixture into an equivalent amount of stirred aqueous ammonia, amine or alkali or alkaline earth metal hydroxide. The pH of the resuting emulsion is adjusted to 8 to 9 with additional aqueous sodium hydroxide. The organic solvents are then removed by distillation to yield a concentrated aqueous solution of the sodium salt of the sulfated condensation product. The ionic group of the surface active condensation product prepared as described above is the sulfate ion, the most hydrophilic of the anionic functional groups. It is especially useful in the formulation of compositions for the treatment of hair and skin because of its minimal tendencies to complex with metal ions and its minimal sensitivity to hard water.

While the soil removal efficiency of the sulfated compounds of this invention makes them suitable for use in the formulation of aqueous hair shampoo compositions, it is necessary to enhance their foaming properties by the inclusion of low-irritating foam promoters taken from the group consisting of amine oxides of the general formula:

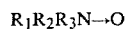

$R_1R_2R_3N \rightarrow O$

The arrow is a conventional representation of a semipolar bond. These compounds are generally prepared by the direct oxidation of the appropriate tertiary amine. When $R_1$ is a much longer chain than $R_2$ and $R_3$, the amine oxides have surface activity. For the purpose of this invention $R_1$ is an alkyl group having from 10 to 16 carbon atoms. Desirable surface active properties are lost if $R_1$ is substantially less than 10 carbon atoms, and the compounds are insufficiently soluble if $R_1$ is greater than 16 carbon atoms. $R_2$ and $R_3$ are each selected from the group consisting of methyl and ethyl groups. Preferably $R_1$ is a dodecyl group or a mixture of dodecyl with decyl, tetradecyl and hexadecyl, such that at least 50% of the groups are dodecyl groups. $R_2$ and $R_3$ are preferably methyl groups. A prefered amine oxide for the purpose of this invention is dodecyldimethylamine oxide.

We have found that in general from about 10 to 20% of the sulfated condensation product should be employed along with about 5 to 15% of the foam promoter. Conventional shampoo adjuvants may, of course, be employed in the formulation of shampoo compositions of this invention including other anionic, nonionic, or ampholytic surface active agents useful in modifying cleansing and foaming properties as well as thickeners, perfumes, dyes and the like.

EXAMPLE I

To a three-neck flask equipped with stirrer, thermometer, dropping funnel and nitrogen inlet tube was added 100 grams (0.10 equivalents of OH) of PLURONIC L-61 (BASF Wyandotte Corp.) a polyoxypropylene-polyoxyethylene copolymer having a molecular weight of approximately 2000 and containing about 10% oxyethylene units on a molar basis. This was followed by the addition of 500 grams of dioxane and 200 ml of methylene chloride. To the dropping funnel was charged 11.6 grams (0.10 mole) of chlorosulfonic acid. The acid was slowly added to stirred solution and cooling applied to maintain a solution temperature of less than 25° C. Upon completion of the addition of the acid, an additional 50 mL of methylene chloride was added to the flask. Then, an additional 1.2 grams of chlorosulfonic acid was added slowly through the dropping funnel. The reaction flask contents were allowed to come to room temperature while being sparged with nitrogen to remove dissolved HCl. The solution of the monosulfuric acid ester of the PLURONIC L-61 was then added to 4 grams of sodium hydroxide dissolved in one L of distilled water. Additional 10% aqueous sodium hydroxide was added to stabilize the pH at 8–9. The methylene chloride and dioxane reaction solvents were removed by distillation to yield an aqueous solution of PLURONIC L-61 monosulfate, sodium salt.

EXAMPLE II

The disulfate, sodium salt of PLURONIC L-61 was prepared following the procedure employed in Example I. Using 100 grams of PLURONIC L-61, the polymer was disulfated with 22.7 grams 0.20 moles) of chlorosulfonic acid. After addition of the acid was complete, an additional charge of methylene chloride was made to the reaction vessel as previously described. Then 2.3 grams additional chlorosulfonic acid was added. After warming to room temperature with a nitrogen sparge, the reaction solution was poured slowly into a solution of 8 grams of sodium hydroxide dissolved in one L of distilled water. Additional 10% aqueous sodium hydroxide was added to stabilize the pH at 8-9. The organic solvents were removed by distillation to give an aqueous solution of PLURONIC L-61 disufate, sodium salt.

EXAMPLE III

The following hair shampoo composition was prepared.

| Ingredient | % by Weight |
|---|---|
| Disulfated PLURONIC L-61, sodium salt | 10.0 |
| Aromox DMC (Akzona Inc.) (a dimethylcocoamine oxide) | 10.0 |
| Perfume, preservative, color and water | q.s. to 100 |

The above shampoo was tested for soil removal efficiency (a measure of the cleansing power of the shampoo) and compared with the efficacy of its individual components as well as a commercial baby shampoo. The results are shown below.

| Shampoo System | % Soil Removal Efficiency at 2.0% Concentration |
|---|---|
| Disulfated PLURONIC L-61 | 24 |
| Aromox DMC | 28 |
| Shampoo of Example III | 33 |
| Commercial Baby Shampoo | 30 |

The soil removal efficiencies exhibit a synergistic effect in the use of the mixture containing both the sulfated PLURONIC and the dimethylcocoamine foam promoter. Evaluation of the shampoo composition by panelists in a blind comparison test showed the shampoo to be effective in cleaning, lather, rinsing, appearance and feel. A persistant talc-like effect was noted on the skin and hair. Rabbit eye irritancy tests showed the sulfated PLURONIC shampoo system to be of low irritation potential comparable to commercial baby shampoos.

EXAMPLE IV

| Ingredient | % by Weight |
|---|---|
| Disulfated PLURONIC L-101, sodium salt | 10.0 |
| Ammonyx CDO (Akzona Inc.) (a cocoamido propyl dimethylamine oxide) | 10.0 |
| Perfume preservative, color and water | q.s. to 100 |

EXAMPLE V

| Ingredient | % by Weight |
|---|---|
| Monosulfated PLURONIC L-31, sodium salt | 10.0 |
| Aromox DMC | 10.0 |
| Perfume, preservative, color and water | q.s. to 100 |

Each of the above two examples when employed as a hair shampoo provides the hair with adequate cleansing, manageability and cosmetic appearance with the benefit of a low level of skin and eye irritation.

Having thus described the invention, what is claimed is:

1. An aqueous hair shampoo composition containing about 10 to 20% by weight of (1) an anionic surface active agent comprising an ammonium, amine or alkali or alkaline earth metal salt of a sulfated condensation product of ethylene oxide with a base formed by condensing propylene oxide with propylene glycol and having a molecular weight of about 1100 to 4800, said condensation product having the structure:

$$HO-(C_2H_4O)_x(C_3H_6O)_y(C_2H_4O)_z-H$$

where y is an integer from about 30 to 70, and $(C_2H_4O)_{x+z}$ equals about 5 to 20% of the total weight of the compound, in combination with (2) about 5 to 15% by weight of a foam promoter comprising an amine oxide of the general formula:

$$R_1R_2R_3N \rightarrow O$$

wherein $R_1$ is an alkyl group containing from about 10 to 16 carbon atoms and $R_2$ and $R_3$ are each selected from the group consisting of methyl and ethyl groups.

2. An aqueous hair shampoo composition as described in claim 1 in which y is an integer from about 40 to 60.

3. An aqueous hair shampoo composition as described in claim 1 in which $(C_2H_4O)_{x+z}$ equals about 7 to 13% of the total weight of the compound.

4. An aqueous hair shampoo composition as described in claim 1 in which said condensation product of ethylene oxide with a base formed by condensing propylene oxide with propylene glycol has been reacted with 0.5 to 2.0 moles of sulfating agent per mole of condensation product.

5. An aqueous hair shampoo composition as described in claims 1, 2, 3, or 4 in which said amine oxide is dodecyldimethylamine oxide.

* * * * *